United States Patent
Rakshit et al.

(10) Patent No.: US 10,915,928 B2
(45) Date of Patent: Feb. 9, 2021

(54) PRODUCT SOLUTION RESPONSIVE TO PROBLEM IDENTIFICATION

(71) Applicant: INTERNATIONAL BUSINESS MACHINES CORPORATION, Armonk, NY (US)

(72) Inventors: Sarbajit K. Rakshit, Kolkata (IN); Craig M. Trim, Ventura, CA (US); John M. Ganci, Jr., Raleigh, NC (US); James E. Bostick, Cedar Park, TX (US); Martin G. Keen, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 114 days.

(21) Appl. No.: 16/191,704

(22) Filed: Nov. 15, 2018

(65) Prior Publication Data

US 2020/0160399 A1    May 21, 2020

(51) Int. Cl.
| | |
|---|---|
| *G06Q 30/02* | (2012.01) |
| *G10L 15/26* | (2006.01) |
| *A61B 5/16* | (2006.01) |
| *G06K 9/00* | (2006.01) |
| *G10L 15/22* | (2006.01) |

(52) U.S. Cl.
CPC ......... *G06Q 30/0271* (2013.01); *A61B 5/165* (2013.01); *G06K 9/00664* (2013.01); *G10L 15/26* (2013.01); *G10L 2015/228* (2013.01)

(58) Field of Classification Search
CPC .............. G06Q 30/0271; G10L 15/26; G10L 2015/228; G06K 9/00664; A61B 5/165
USPC ...................................................... 705/14.67
See application file for complete search history.

(56) References Cited

U.S. PATENT DOCUMENTS

| | | | |
|---|---|---|---|
| 6,466,654 B1 * | 10/2002 | Cooper ................... | G10L 13/00 379/88.01 |
| 9,155,460 B2 | 10/2015 | Steinmetz | |
| 9,345,403 B2 | 5/2016 | Proud | |
| 9,769,166 B1 | 9/2017 | Lai et al. | |

(Continued)

FOREIGN PATENT DOCUMENTS

| | | |
|---|---|---|
| EP | 2096595 A2 | 2/2010 |
| EP | 2096598 A3 | 2/2010 |

OTHER PUBLICATIONS

Repairer Driven News, Fixed Ops Journal, Bosch: AI virtual assistant 'Charlie' could help auto technicians, dated Apr. 17, 2018, downloaded May 5, 2020 from https://www.repairerdrivennews.com/2018/04/17/fixed-ops-journal-bosch-ai-virtual-assistant-charlie-could-help-auto-technicians/ (Year: 2018).*

(Continued)

*Primary Examiner* — Scott D Gartland
(74) *Attorney, Agent, or Firm* — Patrick J. Daugherty; Daugherty & Del Zoppo Co., LPA (57) ABSTRACT

Aspects map biometric data acquired in real-time from a user to a specific task being performed by the user in generating the biometric data; determine that the user is likely experiencing a problem in performing the specific task as a function of a value of the mapped biometric data; determine a performance context of the experienced problem as a function of the mapped biometric data; and select a solution that is most appropriate to solve the experienced problem as a function of the determined performance context and the mapped biometric data.

14 Claims, 4 Drawing Sheets

(56) References Cited

U.S. PATENT DOCUMENTS

| | | | | |
|---|---|---|---|---|
| 10,025,447 | B1* | 7/2018 | Dixit | G06F 9/453 |
| 10,318,001 | B1* | 6/2019 | Spears | G01S 5/0242 |
| 10,685,670 | B2* | 6/2020 | Levi | G10L 25/72 |
| 2011/0263946 | A1* | 10/2011 | el Kaliouby | G06K 9/00335 |
| | | | | 600/300 |
| 2014/0280296 | A1* | 9/2014 | Johnston | G06F 9/453 |
| | | | | 707/769 |
| 2014/0343380 | A1 | 11/2014 | Carter | |
| 2016/0006730 | A1 | 1/2016 | Chari et al. | |

OTHER PUBLICATIONS

Kidd, Chrissy, NLU vs NLP: What's the Difference?, dated May 28, 2018 and downloaded May 5, 2020 from https://www.bmc.com/blogs/nlu-vs-nlp-natural-language-understanding-processing/ (Year: 2018).*

Hutchinson, Andrew, On Facebook's Emotional Ad Targeting, the Manipulation of Younger Users, and the Concerns of Big Data, dated May 3, 2017, downloaded Sep. 30, 2020 from https://www.socialmediatoday.com/ (Year: 2017).*

Lomas, Natasha, Facebook denies it sells ad-targeting based on users' emotions, dated May 2, 2017, downloaded Sep. 30, 2020 from https://techcrunch.com/ (Year: 2017).*

Bharti, P.; Context-Based Human Activity Recognition Using Multimodal Wearable Sensors, Graduate Theses and Dissertations, 2017, entire document, http://scholarcommons.usf.edu/etd/7000.

Anonymous, Weight Quantification Model in the Feature Space for Biometric Evidence, An IP.com Prior Art Database Technical Disclosure, Nov. 5, 2015, entire document, IP.com No. IPCOM000244031D, https://ip.com/IPCOM/000244031.

Anonymous, Method and System for Optimizing Oxygen Levels Based on User's Behavior Biometric Data and Cognitive Profiles, An IP.com Prior Art Database Technical Disclosure, Aug. 30, 2017, entire document, IP.com No. IPCOM000250760D, https://ip.com/IPCOM/000250760.

Anonymous, A Method of Cognitive Social Media Context Management Integrated With a Real Time Biometric Authenticity Service, An IP.com Prior Art Database Technical Disclosure, Feb. 2, 2018, entire document, IP.com No. IPCOM000252697D, https://ip.com/IPCOM/000252697.

Anonymous, Cognitive Prediction of Asthmatic Episodes, An IP.com Prior Art Database Technical Disclosure, May 23, 2018 entire document, IP.com No. IPCOM000253997D, https://ip.com/IPCOM/000253997.

Oakley, J.; Intelligent Cognitive Assistant (ICA) Workshop Summary and Research Needs Collaborative Machine to Enhance Human Capabilities, 2017, https://www.src.org/program/ica, https://www.nsf.gov/nano.

Pato, et al,; Biometric Recognition: Challenges and Opportunities, National Academy of Sciences, 2010, entire document, http://www.nap.edu/catalog.php?record_id=12720.

Peter Mell et al, The NIST Definition of Cloud Computing, National Institute of Standards and Technology, Publication 800-145, 2011, entire document.

* cited by examiner

PRODUCT SOLUTION RESPONSIVE TO PROBLEM IDENTIFICATION

BACKGROUND

Biometric data generally refers to body dimension and physical behavior measurement values and calculations, including those obtained from mobile, wearable and sensor-based devices used while in physical contact or in proximity to a user. Biometric identifiers may be determined from biometric data and refer to distinctive, measurable characteristics used to label and describe individual activity, cognitive state and behavioral characteristics, such as related to patterns of behavior, including but not limited to typing, rhythm, gait, and sleep and voice qualities and patterns.

Sensors within smart watches, smart phones, activity tracking devices and other personal programmable devices carried or worn by a user may determine a variety of physical movement, orientation and location data, including via use of gyroscopes to determine orientation data, accelerometers to determine direction data, altimeters to determine elevation data, and geospatial location processes or components (for example, global positioning satellite (GPS) or cellular or local WiFi signal data processing) to determine precise geographic locations and movements as a function of change of locations over time.

Biometric audio data may include sound data obtained by microphones from user utterances, speech, and other sound-generating activities. Biometric image data generated by user activities may be obtained from video and internal or external cameras in the environment of the user; for example, from cameras internal to a smart phone, smart contact lens, eyeglass devices worn by a user or other person, or cameras located externally to users at vantage points that capture user activities. Examples of physiological biometric data acquired for a user by sensor components include heartbeat, heartrate, respiration amounts or rates or constituent components, blood oxygen, motions, insulin levels, blood sugar levels, etc.

Biometric sensor types include a variety of Internet of Things (IoT), Bluetooth®, or other wired or wireless devices that are personal to the user, and/or incorporated within environments (room, vehicle, home, office, etc.) occupied by the user. Some environmental biometric signal sensors transmit a low-power wireless signal throughout an environment or space occupied by a user (for example, throughout a one- or two-bedroom apartment, inclusive of passing through walls), wherein the signal reflects off of the user's body, and the device uses machine learning to analyze the reflected signals and determine and extract breathing, heart rate, sleep pattern or quality, gait and other physiological, biometric data of the user.

BRIEF SUMMARY

In one aspect of the present invention, a computer implemented method includes mapping biometric data acquired in real-time from a user to a specific task being performed by the user in generating the biometric data; determining that the user is likely experiencing a problem in performing the specific task as a function of a value of the mapped biometric data; determining a performance context of the experienced problem as a function of the mapped biometric data; and selecting a solution that is most appropriate to solve the experienced problem as a function of the determined performance context and the mapped biometric data.

In another aspect, a computer system has a hardware processor in circuit communication with a computer readable memory and a computer-readable storage medium having program instructions stored thereon. The processor executes the program instructions stored on the computer-readable storage medium via the computer readable memory and thereby maps biometric data acquired in real-time from a user to a specific task being performed by the user in generating the biometric data; determines that the user is likely experiencing a problem in performing the specific task as a function of a value of the mapped biometric data; determines a performance context of the experienced problem as a function of the mapped biometric data; and selects a solution that is most appropriate to solve the experienced problem as a function of the determined performance context and the mapped biometric data.

In another aspect, a computer program product has a computer-readable storage medium with computer readable program code embodied therewith. The computer readable program code includes instructions for execution which cause a processor to map biometric data acquired in real-time from a user to a specific task being performed by the user in generating the biometric data; determine that the user is likely experiencing a problem in performing the specific task as a function of a value of the mapped biometric data; determine a performance context of the experienced problem as a function of the mapped biometric data; and select a solution that is most appropriate to solve the experienced problem as a function of the determined performance context and the mapped biometric data.

BRIEF DESCRIPTION OF THE DRAWINGS

These and other features of embodiments of the present invention will be more readily understood from the following detailed description of the various aspects of the invention taken in conjunction with the accompanying drawings in which.

DETAILED DESCRIPTION

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and be rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
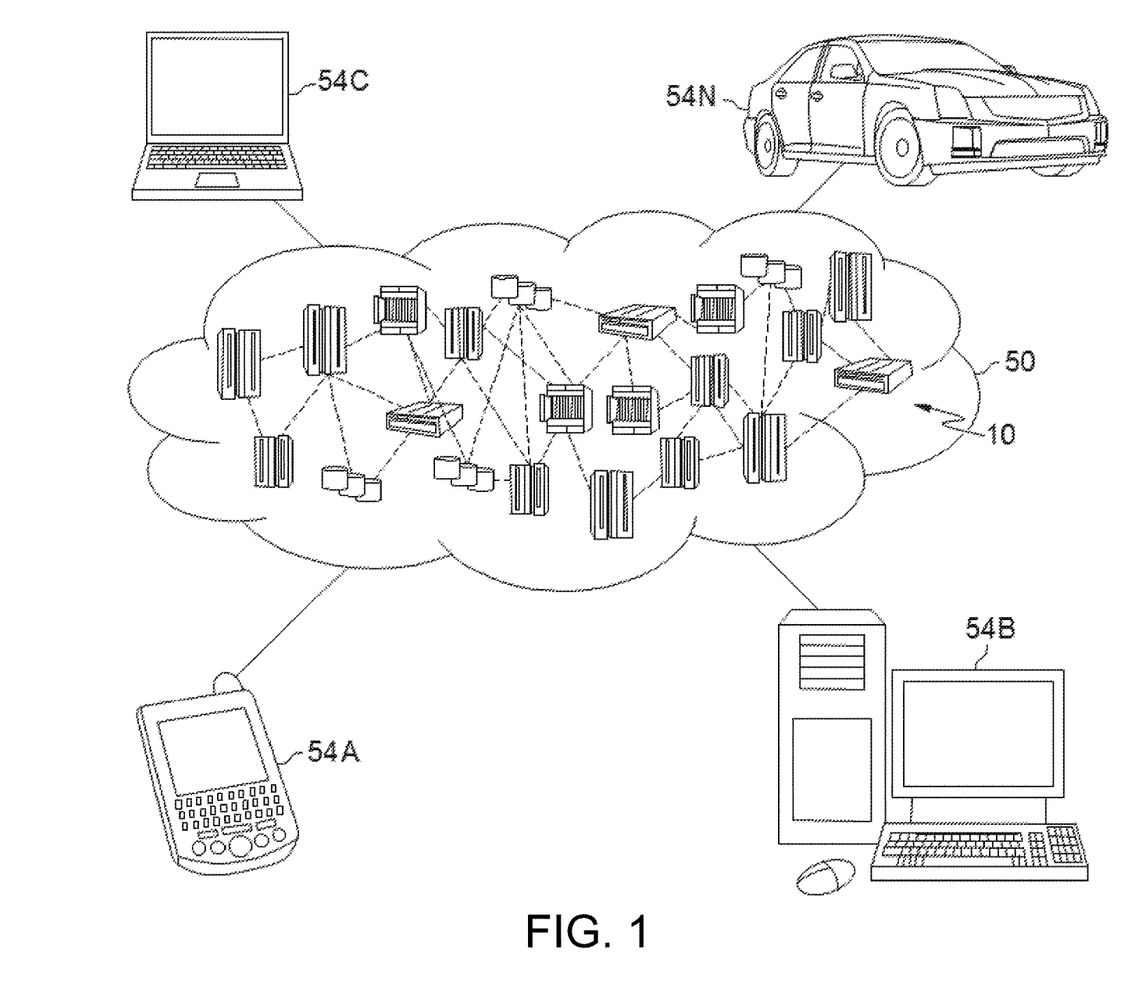
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
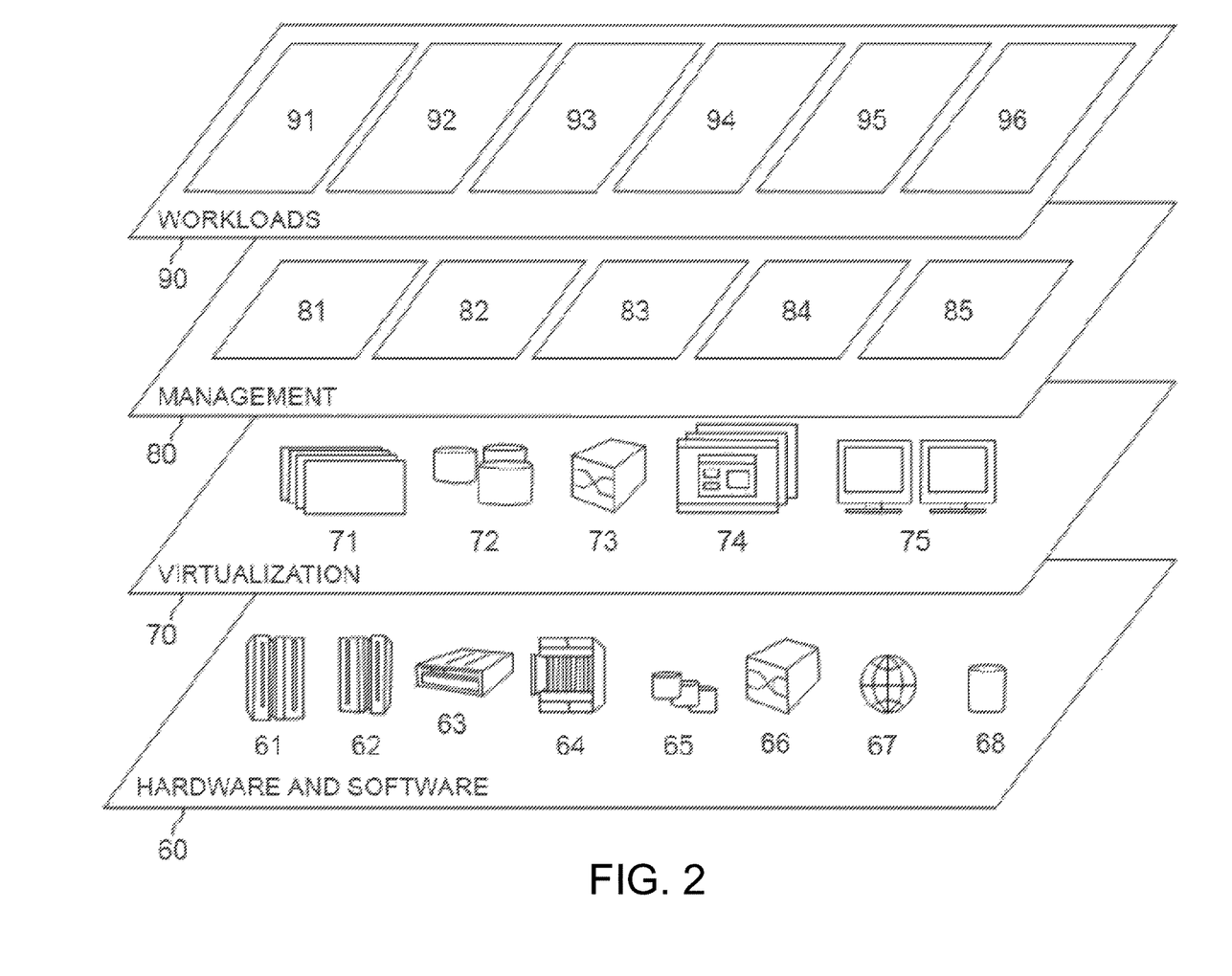
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing 96 according to aspects of the present invention for recommending a solution appropriate to a problem indicated by biometric data.

Figure 3:
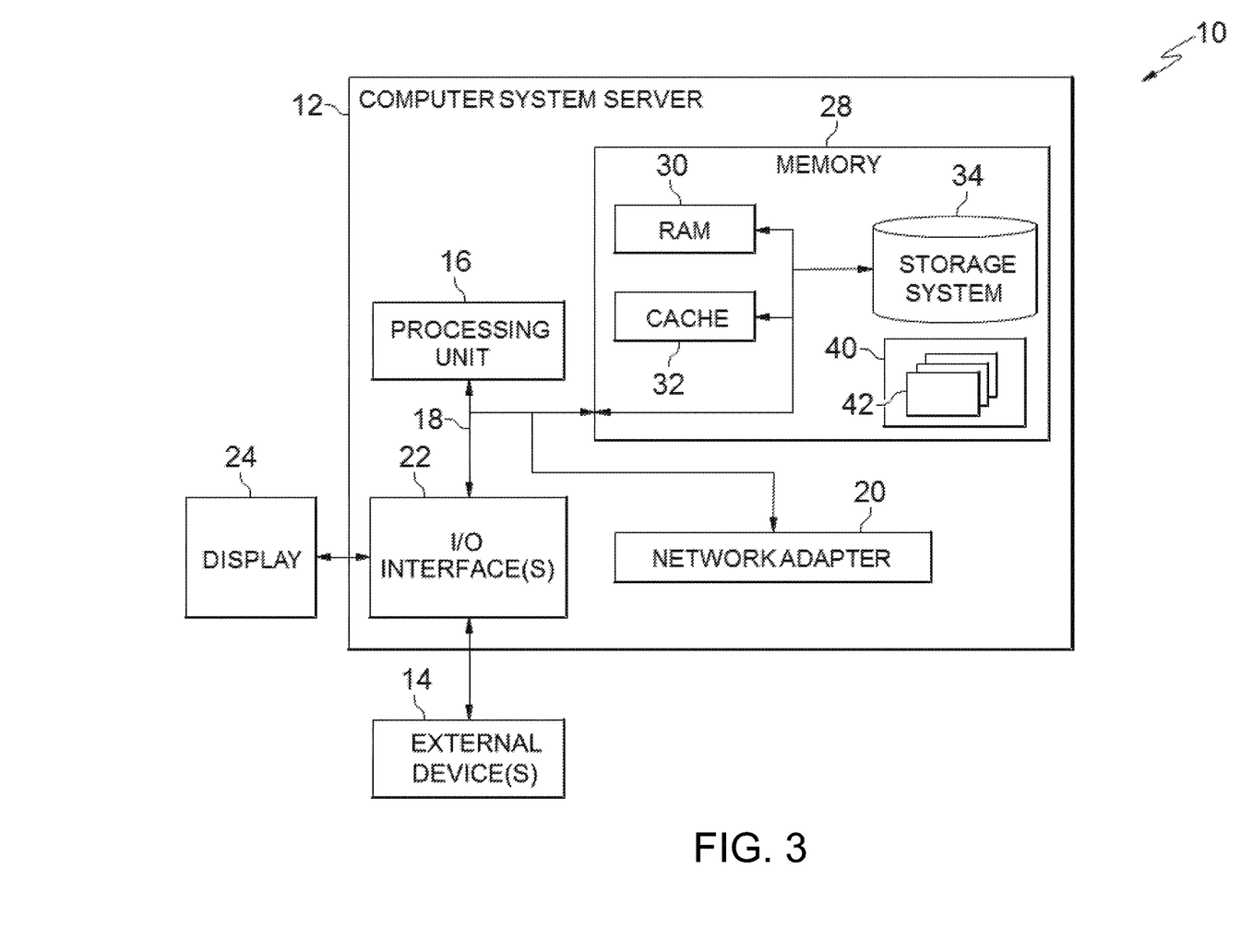
FIG. 3 depicts a computerized aspect according to an embodiment of the present invention.

FIG. 3 is a schematic of an example of a programmable device implementation 10 according to an aspect of the present invention, which may function as a cloud computing node within the cloud computing environment of FIG. 2. Programmable device implementation 10 is only one example of a suitable implementation and is not intended to suggest any limitation as to the scope of use or functionality of embodiments of the invention described herein. Regardless, programmable device implementation 10 is capable of being implemented and/or performing any of the functionality set forth hereinabove.

A computer system/server 12 is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

The computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 4:
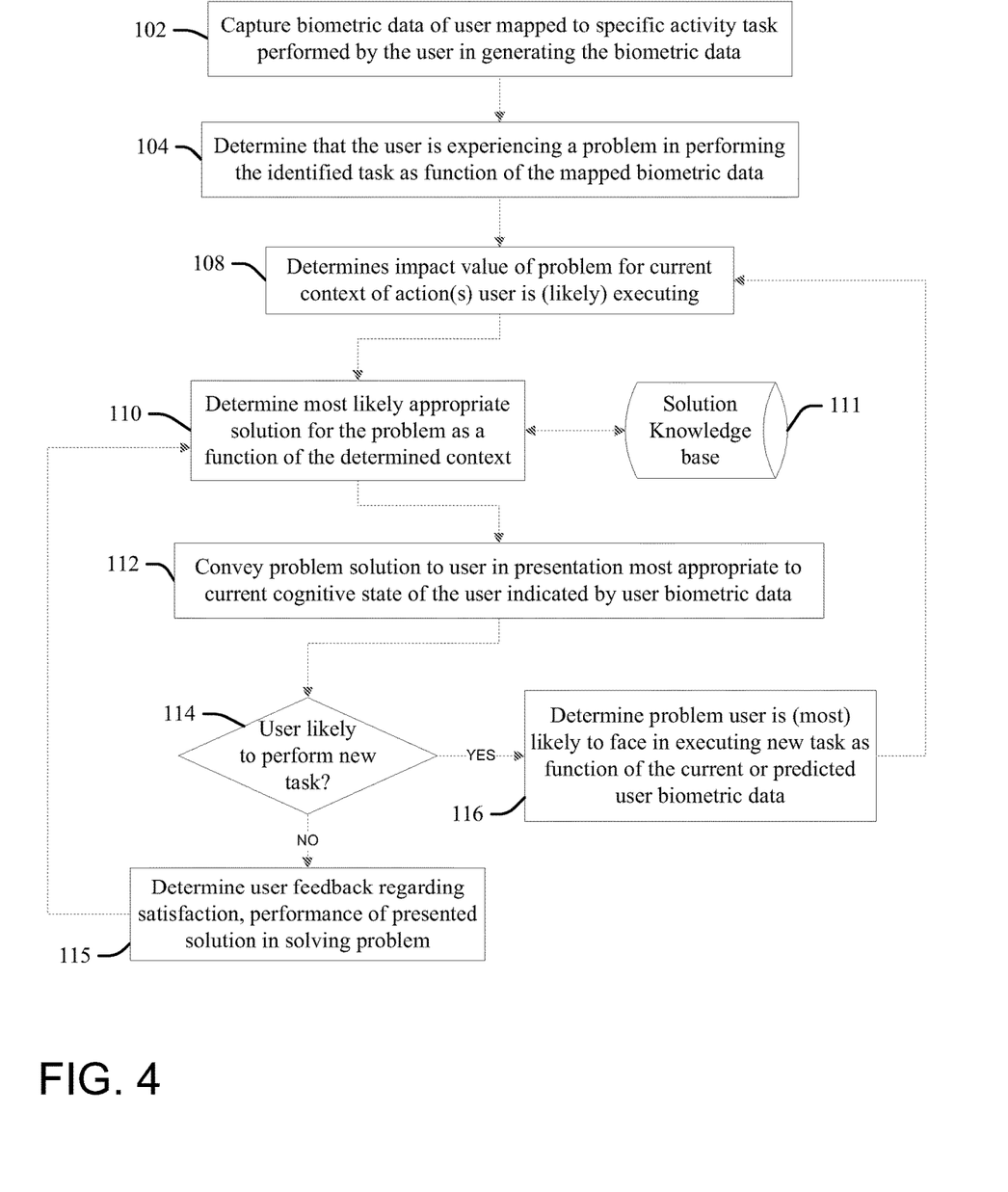
FIG. 4 is a flow chart illustration of an embodiment of the present invention.

FIG. 4 illustrates a system, process or device according to one embodiment of the present invention. At 102 a device processor that is configured according to the present invention (the "configured processor") captures real-time biometric data of a user that is mapped to an identified or specific activity or task performed by the user in generating the biometric data. The configured processor generally obtains data and values (measures) data inclusive of body movements and other physical motion data, gestures, facial expressions (smiles, grimaces, eye reactions and positioning and movements, etc.), auditory statements and outbursts and vocal tones and volumes, heartbeat, heartrate, respiration amounts or rates or constituent components, blood oxygen, motions, insulin levels, blood sugar levels, body temperatures, complexion coloring, etc., that may be indicative of an emotional state of the user executing an activity or task (calm, upset, happy, sad, crying-emotional, etc.) from one or more camera (image), microphone (audio) and biometric sensors in wired or wireless circuit communication with the processor. Illustrative but not exhaustive examples of biometric sensors include cameras or other visual data scanners; microphones and other audio data sensors; wearable devices and sensors, such as smart watches, fitness trackers and other wearable devices, and other devices located near enough to the user to acquire biometric data as a function of signal data received by their sensor components.

Aspects use smart glasses cameras and other wearable devices with outward-facing cameras to capture image data of the user activity, as well as biometric data relevant to a cognitive state of the user, and external cameras, such as used for video conferencing or generally monitoring image data within an environment occupied by the user, in order to thereby capture image data including user motion patterns and facial expressions.

Aspects also use activated microphones or passive listening devices such as smart phones or devices configured to continually monitor for audio signals that include specific task descriptions. In one example the user is performing a braking system maintenance procedure (sometimes herein "a brake job", wherein the embodiment identified the brake job as the task executed by the user in response to text content identified/determined within said audio biometric data (for example, "I am starting to take apart the braking system to determine the cause of the trouble light") by applying natural language processing (NLP) or other text-to-speech processing to identify spoken word text content, and thereby match the identified text content to task descriptions or to text phrasing that is labeled within a dataset as likely associated with a specific task (for example, an "automobile brake system disassembly and rebuild").

Labeled data refers to a group of data samples that have been tagged (via manual, human processes, or via machine learning processes) with one or more meaningful labels or tags that are informative or descriptive of the labelled data, and wherein the labels are used to identify biometric data that matches to the labeled data items. Thus, with respect to the brake job example, a first dataset image of a human manipulating a wrench that is engaged to the underbody of automobile in the vicinity of wheel mounting structures while the wheel is removed has "brake job," "wheel alignment" and "wheel bearing replacement" labels, wherein the configured processor identifies the task from which the biometric data is obtained at 102 as most likely an "automobile brake system disassembly and rebuild" as a function of:

(i) matching gesture image data of the user to the data of the first image (for example, via extracting image data attribute values and matching the extracted values), wherein the task is thereby determined to be likely one of the tasks associated to the first image labels ("brake job," "wheel alignment" and "wheel bearing replacement"); and (ii) determining that the "brake job" task is most likely the correct label/task, as a function of identifying (via NLP processing) that the word "brake" occurs within the speech data of the user more frequently than "alignment" or "wheel bearing", or that a phrase determined within the biometric speech data ("I need a bigger wrench to replace the brake shoes") most strongly matches a phrase labeled as associated to the brake job relative to the other options.

At 104 the configured processor determines that the user is experiencing a problem in performing the task identified at 102 as a function of values of the mapped biometric data. For example, external cameras such as used for video conferencing or generally monitoring image data within a workspace or other environment occupied by the user capture image data including user motion patterns or facial expressions that are matched (via image analysis) to photo or video image data of facial expressions labeled with expressions (grimaces, expressions of pain, dismay, exasperation, displeasure, etc.), or of body movements (for example, video showing both arms raised or swung around rapidly while the person is standing) tagged with labels ("angry," "upset," "frustrated," etc.) that are associated with frustration or problems in executing the task identified at 102.

Embodiments may also use microphones or passive listening devices to obtain and match audio data signals at 104 to dataset signals tagged with labels ("curse word," problematic exclamations, increases in vocal tone or word frequency meeting a threshold change value that is labeled as "upset" "frustrated" audio signal data, etc.) that are associated with frustration or problems in executing the task identified at 102.

Embodiments may also obtain and match at 104 biometric data of changes in heartrates, respiration, facial complexion flushing, vocal tones, etc., to biometric dataset signals tagged with labels associated with an onset of frustration or problems in executing the task identified at 102.

Determining that the user is experiencing a problem at 104 may include determining a specific step or sub-task of the task identified at 102 that is most likely associated with the currently experienced problem as a function of the current, mapped biometric data of the user (determined at 102), and optionally of a context of the mapped data. For example, in response to determining at 102 that the user is driving, the configured processor determines that a current traffic jam environment of the user is most likely causing the current problem indicated by the biometric data (vocal expressions of anger or frustration, rising blood pressure, etc.) as a function of a proportionality of the problem-indicating biometric data values to a decrease in travel speed of the driving user.

In the example of the brake job, at 104 the configured processor analyzes biometric motion data of the user to match to labelled dataset data in order to identify which of a plurality of steps in a knowledge base, standard brake job procedure that the user is currently engaged in, such as removing a brake caliper, installing a new brake rotor, or bleeding a hydraulic brake line, etc.

The user may directly verbalize frustration with a particular step of a given task or activity, wherein audio data sensors capture this data and the configured processor uses NLP processes to identify the matching (or most likely), specific step or sub-task. In the example of the brake job task, the configured processor evaluates known steps, and their precedential relationship to each other, for a knowledge base brake job procedure to identify the step that the user is most likely executing at the time or onset of the determined problem indicators, including as a function of user emotional feedback biometric data: for example, does the biometric data still indicate that the user is currently upset, or is getting more upset?; or, does the data indicate that the user is getting less upset, and therefore that the problem may be resolved?.

At 108 the configured processor determines a degree or value of impact of the problem for a current user context (criticality, difficulty or other attribute) of the actions that the user is currently (likely) executing, as indicated by current biometric data associated to the problem/sub-task. The context attributes may include tools selected and used; lighting, temperature and other environmental factors impacting the comfort or physical abilities of the user (for example, high temperatures and humidity may have negative impact on cognitive attributes including endurance, strength, patience, disposition, calmness, receptiveness to solution presentations or formats thereof, etc.)

At 110 the configured processor determines (selects) a solution for the problem from a Solution Knowledge Base 111 resource or service that is most (likely) appropriate for the determined context and the determined degree of impact of the problem. Some embodiments learn to identify appropriate products to solve user activity problems at 110, wherein the knowledge base 111 is seeded with activities and tasks and associated contexts along with products, service and how to information text and videos, and the effectiveness of a given solution in solving the problem is learned, with results streamed to a cognitive system at 110 to update the knowledge base 111 for future interactions. Embodiments search for the activity and task problems and retrieve products, services or how-to information from the Solution Knowledge Base 111, wherein solutions are associated (labeled) within the knowledge base 111 to different activities and tasks and common problems, and wherein solutions may be directly associated to products or services.

At 112 the configured processor conveys the solution to the user in a presentation that the configured processor selects as (most) appropriate to the current cognitive state of the user (as indicated by or determined from the user biometric data). Presentations are selected in response to determining the most effective communication method to publish or advertise a solution to the user in real-time, including based on availability of the solution, and whether the solution is needed immediately or may instead be deferred to a later, more optimal time. Some embodiment present situational advertisements at 112 to the user in real-time, via a best or preferred, available communication method for the user for the given task or sub-activity, to solve the user problem or simplify the task with how-to information.

Thus, in the brake job example, the configured processor determines at 104 that the user is attempting and failing to loosen a bleed bolt in the step/sub-task to bleeding a hydraulic brake line. At 108 the configured processor further determines that the context of the user efforts includes the user applying a ⅜ inch socket wrench with an eight millimeter socket to loosen the bleed bolt, without a torque limiting component, and wherein the user is not conveying enough rotational force (as estimated by biometric output data) in fear of stripping the bolt (as indicated by spoken text content that is processed via NLP to comprise the phrase "I am afraid I will strip the bolt"). At 110 the configured processor compares this tool selection and application context to a knowledge base procedure and determines that a best practice for the current step/sub-task is to use a torque metric socket wrench that is directly attached to the eight millimeter socket without an adapter, with the torque wrench set to limit the maximum rotation force to a value "X" that is specified to provide enough force to loosen the bolt, without stripping the bolt if the bolt is set firmly in place (due to oxidation, contaminants in thread engagements, etc.) and will not loosen at the "X" force value. Thus, at 112 the configured processor presents a recommendation to the user (via a text message on a graphic user interface (GUI) display, or narration of the text content by a text-to-speech component or process) to use a torque metric socket wrench that is directly attached to the eight millimeter socket without an adapter, with the torque wrench set to limit the maximum rotation force to a value "X".

Aspects of the present invention dynamically select and present problem solutions to the user at 112 that are appropriate to the determined context of the problem (or degree of impact of the problem) and the cognitive state of the user as indicated by the current user biometric data. For example, in response to determining that the biometric data indicates that the user is in a non-agitated cognitive state (for example, only mildly upset, not angry, calm, within a comfortable and well-lit work environment, etc.), the configured processor generates the brake job solution presentation to include an additional text content "explanation" that "the force value of "X" is large enough to loosen the bolt, but still less than the force that will strip the bolt if it is frozen or rusted into place," in response to determining that the cognitive state of the user is likely receptive to the additional explanatory information while in the current biometric state or data status. In contrast, in response to determining that the biometric data indicates that the user is in an agitated cognitive state (angry, hot and sweaty, in an uncomfortable body position to operate a wrench, etc.) the presentation omits said additional text content "explanation," as the user is determined to be unlikely to be patient enough to be receptive to lengthy explanations in a cognitive state associated to the current biometric data values.

While in a non-agitated cognitive state a user is generally more receptive and able to process new information, relative to being in an agitated cognitive state. Embodiments may determine and distinguish between non-agitated cognitive states and agitated cognitive states as a function of determining values of multiple, different types of biometric data inputs. For example, an elevated heart rate may be indicative both of non-agitated cognitive state (for example, of an excited, euphoric or ecstatic state of mind, wherein the user may both open to new ideas and thinking quickly, and hence processing such new ideas efficiently); and an agitated cognitive state (for example, of intense anger or emotional turmoil, wherein the user is not open to considering new subjects or ideas, and unable to focus on and process new subject matters while dwelling on an issue causing the emotional distress). Accordingly, some embodiments consider heart rate data in combination with facial expression data: determining a non-agitated, happy cognitive state from a combination of an elevated heart rate value with extracted image data identified as a "smiling" or "grinning" facial expression; or an agitated, unhappy cognitive state from a combination of the elevated heart rate value with extracted image data identified as a "frowning" or "scowling" facial expression.

Further, ambiguities in determination of the facial expression value may be resolved by considering additional, different biometric data. For example, the embodiment selects or confirms the determination of the non-agitated, happy cognitive state from a combination of the elevated heart rate value with the "smiling" or "scowling" facial expression values and further with audio data values or content including joking words or happy tones or a text content phrase of "I was being sarcastic." In contrast, the embodiment selects or confirms the determination of the agitated, unhappy cognitive state from a combination of the elevated heart rate value with the "smiling" or "scowling" facial expression values and further with audio data values or content including curse words or angry tones.

Embodiments may assign, use and consider a variety of metrics and values in determining and differentiating between agitated and non-agitated cognitive states. For example, embodiments may assign numerical values or weights to differentiate between levels or strengths of emotional state determinations (for example, uneasy=1, mildly upset=2, upset=3, furious=6, etc.), and compare the assigned value, or a sum of a combination of considered different biometric data values, to an "agitated cognitive state threshold" (thus, determining the agitated cognitive state if the total meets the threshold, and otherwise determining a non-agitated cognitive state.

Embodiments may also adjust or reweight biometric value determinations in response to determining deviations within other biometric data from baseline or expected values. For example, in response to determining a deviation from a baseline resting HR measurement, and responsive to further determining that the value exceeds a threshold deviation (for example, shows a recent 20% HR increase), embodiment may increase the emotional state determination values described above by one value for every standard deviation value (for example, bumping "uneasy=1" up to "mildly upset=2").

Some embodiments incorporates learning processes to adjust performance to user tendencies in response to outputs of previous iterations. Thus, in the present example of FIG. 4, at 114 the configured processor determines (predicts) whether it is likely that the user is about to perform a new, identified (second) activity or task as a function of the current biometric data; if not, the configured processor moves on to determine user feedback at 115 regarding satisfaction, performance of presented solution in solving problem, for use in learning improved problem and solution matching in subsequent iterations of 110.

Aspects use feedback to learn the effectiveness of each presented and selected solution in solving a problem (via feedback from the user at 115), and update the knowledge base 111 accordingly with value and weights used to match solution and problem in future interactions at 110. Feedback data may be acquired from mobile and wearable biometric data sensors, in order to confirm that the solution provided has solved the user problem (for example, the user becomes calm, or frustration or anger indicators dissipate). This information is used in learning the effectiveness of product or service solutions, or presentations thereof (including of specific product advertisements), how-to information provided, etc.

In response to determining at 114 that the user is about to perform a new, identified (second) activity or task as a function of the current biometric data, at 116 the configured processor determines what problem the user is (most) likely to face in executing a step or sub-task of the new task as a function of the current or predicted biometric data of the user, and returns to 108 to determine a user context or degree of impact of the predicted problem, determine a solution for the predicted problem as a function of the determined or predicted context at 110, and at 112 convey the solution determined for the predicted problem of the likely new (second) task, sub-task to the user in a presentation selected as (most) appropriate to the current or predicted cognitive state of the user (as indicated by the current or likely, predicted user biometric data). For example, the configured processor presents an appropriate advertisement as a solution at 112 that is delivered to the user with a reference of a past experience of a similar problem and an explanation as to why this solution will satisfy the predicted problem (in view of the success of a similar solution for the similar problem in the past).

Returning to the brake job example, the configured processor predicts at 114 that the user, or group of users with which the present user shares demographic data values, will next perform a front-end alignment on the vehicle, as this user (or group member) follows brake jobs with front-end alignments with an 80% percent frequency, or recent data indicates that wheel alignment problems arise 80% of the time in association with this brake job for vehicles having current data (make and model, year of model, elapsed mileage since last alignment, etc.); predicts at 116 that the user will have difficulty in the step of removing a rocker-arm to inspect a bushing in performing the front-end alignment, as this happens in 60% of front-end alignments performed by the user (or for this data make and model, year of model, elapsed mileage since last alignment, etc.); predicts at 108 that user context or degree of impact of the predicted problem will be an increase in frustration levels relative to current biometric data (due to increasingly falling behind a time schedule for completing both the brake job and predicted, subsequent wheel alignment; as a function of the user historic frustration indicators associated with similar, current biometric data, etc.); determines at 110 that the most-likely solution is to use a most appropriate, specific tool "Y" for removal of the rocker arm (as it typically results in a significant time savings or using another tool "Z" that is typically used for the user); and at 112 presents an audio recitation of content to the user "Joe" of "Hey Joe, I recommend you get tool Y before you begin aligning the front-end," as a function of predicting that the cognitive state of the user will be receptive to the colloquial address style ("Hey Joe, . . . ") of the presentation, as indicated by the likely user biometric data (that Joe will be frustrated, perhaps upset but unlikely to be angry at this point in time).

In another example, an embodiment determines that a user is in a frustrated cognitive state (as indicated by biometric data), and responsively determines that the user is in a vehicle that is stuck in a traffic jam, and further determines that the context of the current status includes a failure to use a sophisticated mapping application that is enabled to recommend alternative routing, which resulted in the user being unaware of construction delays on the current, chosen route leading to the user location within the traffic jam. In response, the embodiment identifies as a solution and presents an advertisement to the user for a comprehensive mapping and routing application that dynamically creates optimum routes in response to real-time road, traffic and weather conditions. Said presentation is configured in a format appropriate to the current user context and cognitive state (for example, in a text-to-speech presentation located between songs of a music stream playing over speakers in the vehicle, or in a bulletin displayed on a navigation screen on the user dashboard, or in a text message to a smart phone linked to the vehicle entertainment or information system, etc.) to thereby make the user aware of the problem and possible solution to solve the current situation, and to prevent problems for future travel needs as well, in a format that is likely acceptable to the user in the determined cognitive state of the user.

Aspects of the present invention determine if a user has a problem with their current activity from analysis of wearable "digital exhaust data." Once a problem or struggle with the current activity is recognized or determined, aspects present the user with advertisements of products or services, or how-to knowledge to solve the problem identified that are appropriate to context and cognitive state of the user. For example, advertisement presentments of products or services to the user may be via web click stream or similar methodology that are preferred by the user as determined from historic user viewing or previous purchase activity; or via targeted broadcast media (television, radio, streaming content channel, etc.) marketing to preferred programming; through email communications in a format and frequency determined to be acceptable to the user, wherein the user will read the email rather than delete as spam; and via inclusion in how-to information search results obtained from Internet, video service or social network application searching.

Aspects provide advantages over prior art marketing based on user purchase or viewing activity, as said prior art teachings do not revise or alter marketing presentation in response to real-time determinations or recognitions of problems or struggles that a user is currently experiencing with physical activities, or to their current cognitive state while experiencing the struggle, which results in failure to reach the user when the presentation is not appropriate to said current struggle and cognitive state. Prior art advertisement presentations are generally based on activity topic, and cannot identify specific problems or struggles the user is currently having, but rather must focus more broadly on a general topic, and thus, are less likely to be relevant to the current needs of the struggling user.

The terminology used herein is for describing aspects only and is not intended to be limiting of the invention. As used herein, singular forms "a", "an", and "the" are intended to include the plural forms as well, unless the context clearly indicates otherwise. It will be further understood that the terms "include" and "including" when used in the specification specify the presence of stated features, integers, steps, operations, elements, and/or groups thereof. Certain examples and elements described in the present specification, including in the claims, and as illustrated in the figures, may be distinguished, or otherwise identified from others by unique adjectives (e.g. a "first" element distinguished from a "second" or "third" of a plurality of elements, a "primary" distinguished from a "secondary" one or "another" item, etc.) Such identifying adjectives are generally used to reduce confusion or uncertainty and are not to be construed to limit the claims to any specific illustrated element or embodiment, or to imply and precedence, ordering, or ranking of any certain elements, limitations, or process steps.

The descriptions of the carious embodiments of the present invention have been presented for the purposes of illustration but are not intended to be exhaustive or limited to the embodiments disclosed. Many modifications and variations will be apparent to those of ordinary skill in the art without departing for the scope and spirit of the described embodiments. The terminology used herein was chosen to best explain the principles of the embodiments, the practical applications or technical improvement over technologies found in the marketplace, or to enable others of ordinary skill in the art to understand the embodiments disclosed herein.

What is claimed is:

1. A computer-implemented method, comprising:
mapping biometric data acquired in real-time from a user to a specific task being performed by the user in generating the biometric data;
determining that the user is likely experiencing a problem in performing the specific task as a function of a value of the mapped biometric data;
determining a performance context of the experienced problem as a function of the mapped biometric data;
determining a current cognitive state of the user while experiencing the problem as a function of the mapped biometric data, wherein the current cognitive state is selected from a plurality of cognitive states that comprises an agitated state and a calm state;
selecting from a plurality of solutions a solution that is most appropriate to solve the experienced problem relative to others of the plurality of solutions as a function of the determined performance context and the current cognitive state; and
presenting the selected solution to the user as a function of the current cognitive state, said presenting comprising:
in response to determining that the current cognitive state of the user is the calm state, presenting the selected solution with additional explanation text content that explains why the selected solution will solve the experienced problem; and
in response to determining that the current cognitive state of the user is the agitated state, presenting the selected solution without presenting the additional explanation text content.

2. The method of claim 1, further comprising:
presenting the selected solution in an advertisement presentment that is preferred by the user as a function of historic user activity, wherein the advertisement presentment is selected from the group consisting of an email communication, a search result, and a broadcast media marketing advertisement.

3. The method of claim 1, further comprising:
predicting whether it is likely that the user is about to perform a predicted new task at a future time as a function of the performance context of the experienced problem and demographic data values of the user, wherein the predicted new task is different from the specific task;
determining a predicted problem that the user is likely to face in executing the predicted new task at the future time as a function of predicted biometric data of the user at the future time and the demographic data values of the user; and
presenting a predicted solution to the user that is likely appropriate to solve the predicted problem in execution of the predicted new task as a function of the predicted user context of execution and the demographic data values of the user.

4. The method of claim 1, further comprising:
extracting image data from the mapping biometric data that comprises a plurality of user motion patterns;
identifying the specific task being performed by the user in generating the biometric data by matching a first of the extracted image data user motion patterns to a knowledge base motion pattern that is labeled as the specific task; and
determining that the user is likely experiencing the problem in performing the specific task by matching the biometric data mapped to performing the specific task to a knowledge base biometric data value that is labeled as an expression of frustration.

5. The method of claim 4, wherein the specific task comprises a plurality of sub-tasks, the method further comprising:

transforming speech content within an audio signal of the mapped biometric data into biometric data text content via natural language processing;

determining that the experienced problem is associated with a first of the sub-tasks in response to determining that the biometric data text content is more strongly associated with the first sub-task relative to remaining others of the plurality of sub-tasks.

6. The method of claim 1, further comprising:

integrating computer-readable program code into a computer system comprising a processor, a computer readable memory in circuit communication with the processor, and a computer readable storage medium in circuit communication with the processor; and wherein the processor executes program code instructions stored on the computer-readable storage medium via the computer readable memory and thereby performs the mapping the biometric data to the specific task being performed by the user in generating the biometric data, the determining that the user is likely experiencing the problem in performing the specific task as a function of the value of the mapped biometric data, the determining the performance context of the experienced problem as a function of the mapped biometric data, the determining the current cognitive state of the user, the selecting the solution, and the presenting the selected solution.

7. The method of claim 6, wherein the computer-readable program code is provided as a service in a cloud environment.

8. A computer system, comprising:

a processor;

a computer readable memory in circuit communication with the processor; and a computer readable storage medium in circuit communication with the processor;

wherein the processor executes program instructions stored on the computer-readable storage medium via the computer readable memory and thereby:

maps biometric data acquired in real-time from a user to a specific task being performed by the user in generating the biometric data;

determines that the user is likely experiencing a problem in performing the specific task as a function of a value of the mapped biometric data;

determines a performance context of the experienced problem as a function of the mapped biometric data;

determines a current cognitive state of the user while experiencing the problem as a function of the mapped biometric data, wherein the current cognitive state is selected from a plurality of cognitive states that comprises an agitated state and a calm state;

selects from a plurality of solutions a solution that is most appropriate to solve the experienced problem relative to others of the plurality of solutions as a function of the determined performance context and the current cognitive state; and presents the selected solution to the user as a function of the current cognitive state, wherein:

in response to determining that the current cognitive state of the user is the calm state, the processor presents the selected solution with additional explanation text content that explains why the selected solution will solve the experienced problem; and in response to determining that the current cognitive state of the user is the agitated state, the processor presents the selected solution without presenting the additional explanation text content.

9. The system of claim 8, wherein the processor executes the program instructions stored on the computer-readable storage medium via the computer readable memory and thereby:

presents the solution in an advertisement presentment that is preferred by the user as a function of historic user activity, wherein the advertisement presentment is selected from the group consisting of an email communication, a search result, and a broadcast media marketing advertisement.

10. The system of claim 8, wherein the processor executes the program instructions stored on the computer-readable storage medium via the computer readable memory and thereby:

predicts whether it is likely that the user is about to perform a predicted new task at a future time as a function of the performance context of the experienced problem and demographic data values of the user, wherein the predicted new task is different from the specific task;

determines a predicted problem that the user is likely to face in executing the predicted new task at the future time as a function of predicted biometric data of the user at the future time and the demographic data values of the user; and presents a predicted solution to the user that is likely appropriate to solve the predicted problem in execution of the predicted new task as a function of the predicted user context of execution and the demographic data values of the user.

11. The system of claim 8, wherein the specific task comprises a plurality of sub-tasks, and wherein the processor executes the program instructions stored on the computer-readable storage medium via the computer readable memory and thereby:

extracts image data from the mapping biometric data that comprises a plurality of user motion patterns;

identifies the specific task being performed by the user in generating the biometric data by matching a first of the extracted image data user motion patterns to a knowledge base motion pattern that is labeled as the specific task;

determines that the user is likely experiencing the problem in performing the specific task by matching the biometric data mapped to performing the specific task to a knowledge base biometric data value that is labeled as an expression of frustration;

transforms speech content within an audio signal of the mapped biometric data into biometric data text content via natural language processing; and determines that the experienced problem is associated with a first of the sub-tasks in response to determining that the biometric data text content is more strongly associated with the first sub-task relative to remaining others of the plurality of sub-tasks.

12. A computer program product, comprising:

a computer readable storage medium having computer readable program code embodied therewith, the computer readable program code comprising instructions for execution by a processor that cause the processor to:

map biometric data acquired in real-time from a user to a specific task being performed by the user in generating the biometric data;

determine that the user is likely experiencing a problem in performing the specific task as a function of a value of the mapped biometric data;

determine a performance context of the experienced problem as a function of the mapped biometric data;

determine a current cognitive state of the user while experiencing the problem as a function of the mapped biometric data, wherein the current cognitive state is selected from a plurality of cognitive states that comprises an agitated state and a calm state;

select from a plurality of solutions a solution that is most appropriate to solve the experienced problem relative to others of the plurality of solutions as a function of the determined performance context and the current cognitive state; and present the selected solution to the user as a function of the current cognitive state, wherein:

in response to determining that the current cognitive state of the user is the calm state, the processor presents the selected solution with additional explanation text content that explains why the selected solution will solve the experienced problem; and in response to determining that the current cognitive state of the user is the agitated state, the processor presents the selected solution without presenting the additional explanation text content.

13. The computer program product of claim 12, wherein the computer readable program code instructions for execution by the processor further cause the processor to:

predict whether it is likely that the user is about to perform a predicted new task at a future time as a function of the performance context of the experienced problem and demographic data values of the user, wherein the predicted new task is different from the specific task;

determine a predicted problem that the user is likely to face in executing the predicted new task at the future time as a function of predicted biometric data of the user at the future time and the demographic data values of the user; and select a predicted solution that is likely appropriate to solve the predicted problem in execution of the predicted new task as a function of the predicted user context of execution and the demographic data values of the user.

14. The computer program product of claim 12, wherein the specific task comprises a plurality of sub-tasks, and wherein the computer readable program code instructions for execution by the processor further cause the processor to:

extract image data from the mapping biometric data that comprises a plurality of user motion patterns;

identify the specific task being performed by the user in generating the biometric data by matching a first of the extracted image data user motion patterns to a knowledge base motion pattern that is labeled as the specific task;

determine that the user is likely experiencing the problem in performing the specific task by matching the biometric data mapped to performing the specific task to a knowledge base biometric data value that is labeled as an expression of frustration;

transform speech content within an audio signal of the mapped biometric data into biometric data text content via natural language processing; and determine that the experienced problem is associated with a first of the sub-tasks in response to determining that the biometric data text content is more strongly associated with the first sub-task relative to remaining others of the plurality of sub-tasks.

\* \* \* \* \*